United States Patent
Bruder et al.

(10) Patent No.: US 8,422,625 B2
(45) Date of Patent: Apr. 16, 2013

(54) MOTION CONTROL METHOD AND MOTION CONTROL MODULE, IMAGE PROCESSING ACTUATION METHOD AND IMAGE PROCESSING ACTUATION MODULE

(75) Inventors: Herbert Bruder, Höchstadt (DE); Rainer Raupach, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 432 days.

(21) Appl. No.: 12/585,575

(22) Filed: Sep. 18, 2009

(65) Prior Publication Data

US 2010/0074398 A1    Mar. 25, 2010

(30) Foreign Application Priority Data

Sep. 19, 2008    (DE) .................. 10 2008 048 034

(51) Int. Cl.
    *A61B 6/03*    (2006.01)
(52) U.S. Cl.
    USPC ............................................................ 378/8
(58) Field of Classification Search ............... 378/8, 95; 600/428
    See application file for complete search history.

(56) References Cited

U.S. PATENT DOCUMENTS

| 2004/0077941 A1* | 4/2004 | Reddy et al. ............... 600/428 |
| 2007/0121780 A1 | 5/2007 | Watanabe |
| 2008/0165919 A1* | 7/2008 | Bruder et al. ................ 378/8 |

FOREIGN PATENT DOCUMENTS

DE    102006056997 A1    5/2007

* cited by examiner

*Primary Examiner* — Glen Kao
(74) *Attorney, Agent, or Firm* — Harness, Dickey & Pierce, P.L.C.

(57) ABSTRACT

A motion control method is disclosed for controlling a relative scan feed motion of an object bearing device toward a scanner unit of a computed tomography system. Here, scan motion control signals are generated parallel to the scan feed motion for controlling the scan feed motion, which scan motion control signals are derived from variable input data obtained in parallel during a scan procedure. In at least one embodiment, the variable input data includes motion signals which represent the object motion cycle determined with the aid of an electrocardiogram, and the speed of the scan feed motion is reduced if an extrasystole is detected. Furthermore, at least one embodiment of the invention relates to a motion control module suited to this and/or an image processing actuation method and/or an image processing actuation module for actuating an image processing system.

21 Claims, 3 Drawing Sheets

MOTION CONTROL METHOD AND MOTION CONTROL MODULE, IMAGE PROCESSING ACTUATION METHOD AND IMAGE PROCESSING ACTUATION MODULE

PRIORITY STATEMENT

The present application hereby claims priority under 35 U.S.C. §119 on German patent application number DE 10 2008 048 034.7 filed Sep. 19, 2008, the entire contents of which are hereby incorporated herein by reference.

FIELD

At least one embodiment of the present invention generally relates to a motion control method and/or a motion control module for controlling a relative scan feed motion of an object bearing device toward a scanner unit of a computed tomography system during a helical tomography scan. At least one embodiment also generally relates to an image processing actuation method and/or an image processing actuation module for actuating an image processing system of a computed tomography system, in which raw image data acquired during operation by the computed tomography system and/or image data of an examination object carrying out a cyclical object motion derived therefrom are processed.

BACKGROUND

Relative scan feed motions of object bearing devices toward scanner units of computed tomography systems, which are usually referred to as a so-called feed, are usual in the daily routine of computed tomography system operation. This motion should be distinguished from the scan rotational motion of an X-ray radiation source and an X-ray detector of the computed tomography scanner, which rotate around an object bearing device with an examination object borne thereon, e.g. an organ of a human body. The scan feed motion is generally directed perpendicularly to the rotational plane defined by the scan rotational motion.

In a helical tomography scan, an examination object is continuously moved relative to the encircling annulus of the X-ray radiation source during an irradiation. Hence, the scan rotational motion and the scan feed motion are combined such that the examination object is irradiated in a helical shape.

Here, the feed is used to be able to ensure complete coverage of an examination object. This is particularly necessary in the case of relatively large examination objects combined with detection regions which cannot acquire the whole examination object at once. During the feed, either the object bearing unit or the scanner unit is moved in the direction of the respectively other element, or both units are moved toward or away from each other.

In general, such a relative scan feed motion is a linear motion, i.e. it is effected at a constant speed and unchanging motion direction. However, in specific cases, e.g. a repeated helical scan by a computed tomography system, the scan feed motion can be repeated a number of times, i.e. the object bearing device and/or the scanner unit are retracted into their initial position once a run-through is complete and the motion process is repeated iteratively a number of times.

However, in the case of tomography scans, in particular computed tomography scans, it can often be the case that external or internal interference becomes noticeable during the scan, as a result of which parts of the acquired image data, or image data which can be acquired, cannot be utilized or can only be utilized badly. By way of example, such interference is due to an operator wishing to influence proceedings during a tomography scan or other influences which specifically depend on the examination object.

These are predominantly motions of the examination object or its surroundings, e.g. insuppressible organ motions of a patient, predominantly the heart rate or lung motion, which are both transferred to other regions of the body as well. In the case of a regular cyclical motion such influencing factors can be artificially eliminated during the tomography scan or in the following procedures. This is effected by way of so-called prospective or retrospective "triggering" or "gating". In both methods, time corridors are fixed during which the cyclical motion is in a phase of relative rest, e.g. in the transition from respiration to aspiration in the breathing curve or during the first half of the diastole in the cardiac curve. In the case of prospective triggering or gating, raw image data is only acquired within such time corridors, whereas in retrospective triggering or gating only those parts of the generally continuously acquired raw image data which were acquired during such time corridors are continued to be used for imaging optimized processing.

By contrast, in the case of irregular motion, there is only limited scope for such a correction by triggering or gating and so there is the risk that parts of the acquired image data are worthless for the further examination. In particular, the feed during the scanning procedure within the scope of a helical tomography scan leads to only a very limited amount of raw image data being acquired for a certain tissue volume. If such an irregular motion occurs at just that time when a particular tissue region is scanned, it may be the case that no usable image data is available for this region. This problem is increased by the fact that for example the heart rate frequency can in any case change during a scan. The tomography system cannot react to this and therefore the risk of unusable acquired image data is further increased.

DE 10 2006 056 997 A1 proposes that the feed speed of a patient couch during a CT spiral scan is changed in accordance with the changes of a heart rate of a subject lying on the patient couch.

SUMMARY

At least one embodiment of the present invention provides a further improved motion control method or a control system for controlling a relative scan feed motion. Furthermore, at least one embodiment of the present invention permits further improved image acquisition or image processing.

According to various embodiments of the invention, a motion control method, a motion control module, an image processing actuation method and an image processing actuation module are disclosed.

In the case of a motion control method according to an embodiment of the invention, scan motion control signals which are derived from variable input data obtained during the tomography scan for controlling the scan feed motion are generated in parallel to the scan feed motion during a helical tomography scan of a heart carrying out a substantially cyclical object motion. "Variable input data" is understood to mean that the input data is only obtained during the scan procedure unlike control data which is already fixed before the scanning procedure and, for example, is stored in a scan protocol. In accordance with an embodiment of the invention, this variable input data comprises motion signals which represent the object motion cycle determined with the aid of an electrocardiogram. They then serve as a basis for controlling the scan feed motion in the ongoing scan procedure, with the speed of the scan feed motion being reduced if an extrasystole is detected.

The method according to an embodiment of the invention thus provides the decisive advantage that, in addition to the control data which originates from a scan protocol, it is also possible for variable influencing data to be taken into account which, together with non-variable control inputs, is then used in the control of the scan feed motion. This means that the scan feed motion can react to unforeseeable interference by, for example, accelerating or slowing down.

A motion control module, of an embodiment, of analogous design for controlling a relative scan feed motion of an object bearing device toward a scanner unit of a computed tomography system for performing a helical tomography scan of a heart carrying out a substantially cyclical object motion comprises at least:

an input interface for variable input data which comprises motion signals which represent the object motion cycle determined with the aid of an electrocardiogram, a control command generation unit which is designed such that during operation it derives scan motion control signals for controlling the scan feed motion as a function of the variable input data, and an output interface for outputting the scan motion control signals to a control device for the object bearing device and/or the scanner unit, wherein the motion control module is designed such that the speed of the scan feed motion is reduced if an extrasystole is detected.

The specified interfaces do not necessarily have to be designed as hardware components but can also be implemented as software modules, for example if the input data can be transferred to another component implemented on the same equipment, such as an image reconstruction apparatus or the like, or if the input data only has to be transmitted by software to this other component. Likewise, the interfaces can also consist of hardware- and software components, such as a standard hardware interface specifically configured for the particular use by means of software.

Overall, the bulk of the components for implementing the motion control module according to an embodiment of the invention, in particular the control command generation unit, can be implemented in full or in part in the form of software modules on a processor.

It is for this reason that an embodiment of the invention also comprises a computer program product which can be directly loaded into storage of a programmable motion control module, comprising program code sections to execute all steps of a motion control method according to an embodiment of the invention when the program is executed in the motion control module.

An image processing actuation method according to an embodiment of the invention of the type mentioned initially is distinguished by the fact that motion data is recorded which is connected to a relative scan feed motion of an object bearing device toward a scanner unit of a computed tomography system, a motion profile is generated from the motion data, and image processing control signals are generated from the motion profile, which image processing control signals are used as a control input for the image processing system, wherein the scan feed motion is controlled by a motion control method according to an embodiment of the invention.

Hence, the image processing actuation method is used for improved retrospective gating which is flexibly matched to the scan feed motion. The motion data results in a motion profile which is generated only in the ongoing scan operation in contrast to a scan profile fixed in advance in a scan protocol fixed in advance.

Since the scan feed motion within the scope of an embodiment of the invention is effected as a function of the variable input data, both types of data can in end effect be used in a fashion compatible to one another. That is to say, in end effect, the image processing is also effected as a function of the scan feed motion and hence it is automatically taken into account if the scan feed motion is changed as a result of interference. As a result of the image (post) processing, the variations in the scan feed motion can thus again be "removed from the calculation" retrospectively by being included as an influencing factor for fixing gating intervals.

An image processing actuation module according to an embodiment of the invention of the type mentioned initially comprises at least:

an input interface for motion data which is connected to a relative scan feed motion of an object bearing device toward a scanner unit of a computed tomography system, a motion profile generation unit for generating a motion profile from the motion data, a control signal generation unit for deriving image processing control signals from the motion profile, and an output interface for outputting the image processing control signals to the image processing system, wherein the image processing actuation module is coupled to a motion control module according to the invention so as to determine motion data on the basis of the scan motion control signals.

In an analogous fashion to the abovementioned motion control module, it also holds true for the image processing actuation module according to the invention that the interfaces do not necessarily have to be designed as hardware components and that the bulk of the components for its implementation of the image processing control module according to the invention, here in particular the motion profile generation unit and the control signal generation unit, can be fully or partly implemented in the form of software modules on a processor.

It is for this reason that an embodiment of the invention also comprises a computer program product which can be directly loaded into storage of a programmable image processing actuation module, comprising program code sections to execute all steps of an image processing actuation method according to an embodiment of the invention when the program is executed in the image processing actuation module.

Additional particularly advantageous refinements and developments of embodiments of the invention emerge from the dependent claims and the following description. Here the motion control method, the motion control module, the image processing actuation method and the image processing actuation module can also be developed according to the respective dependent claims of the other modules or methods.

In accordance with an example embodiment of the motion control method according to the invention, a dependence of the scan feed motion on the variable input data is fixed in advance in one or more rules. By way of example, one such rule can be stored within a scan protocol or a motion control module according to an embodiment of the invention and have certain differentiations. By way of example, it can comprise different control signals for controlling the scan feed motion on the basis of differentiating characteristics between external and internal interference. This is effected as a function of the type and possibly the intensity of the variable input data. Storing the dependence of the scan feed motion on the variable input data in one or more rules predominantly has the advantage that this can take into account a multiplicity of different input data and that updating, which can be effected easily by software updates for example, is possible. Furthermore, rules can effect a fully automated derivation of scan motion control signals for the scan feed motion from the variable input data.

As already described previously, it is possible for the variable input data to comprise system internal and/or system external input data. By way of example, external input data can relate to inputs by a user of the computed tomography system. The variable input data is particularly preferably derived directly or indirectly from an examination object and/or a body surrounding an examination object. In the field of medical imaging, such a body is generally the body of a creature, in particular a human body, with a specific organ or body region representing the examination object.

It is particularly advantageous to control the scan feed motion as a function of decisive inputs which are generated by the examination object itself. By way of example, a creature has a number of organs, such as the heart and lungs, which are moved directly or indirectly and the body motion of said creature can additionally interfere with imaging. Within the scope of this, a possible central application of the motion control method according to an embodiment of the invention includes the object bearing device bearing an examination object, generally an organ, which carries out substantially cyclical object motion and the variable input data comprising motion signals which represent the cycle of the object motion.

It is particularly preferable for the examination object to be a heart and the cycle is determined with the aid of an electrocardiogram. Particularly in the case of cardiac imaging within the scope of helical tomography scans, it is necessary to take sufficient account of cycle variations during the imaging, or the processing of image data, as indicated above. Thus, it must be ensured that the scan feed motion is only so fast that, within the region covered by one scanner rotation, the heart can be detected over at least 180° of its circumference in a cycle region of its cardiac cycle in which it does not carry out significant motion. Taking account of the cardiac curve as a variable input data in terms of the motion control method according to an embodiment of the invention affords the possibility of adapting the scan feed motion in a partly or fully automated manner such that complete cover of the heart can obtain a complete image of the organ when taking into account the respective detector width of the tomography system and the cycle portions that can be used for gating.

In particular, this holds true even if the cyclic cardiac motion is changed by intermediate deflections, that is to say by irregularities within the cyclical object motion. In that case, provision is advantageously made for a change of the speed of the scan feed motion to be derived, in particular if an extrasystole is detected in a cardiac scan, a reduction in the speed of the scan feed motion being particularly preferred. An extrasystole, that is to say a heartbeat completely outside of the regular cardiac cycle has the effect of the normal cycle only continuing thereafter with a delay. Therefore, the reduction in the speed is used to "intercept" the irregularities in the object motion and thereafter find a new regularity in the object motion on the basis of which the scan feed motion can then in turn be adapted accordingly. This means that a complete stop of the scan feed motion is usually dispensed with and that there is only a delay.

The cycle lengths of the object motion is a further preferred reference variable in the motion control method according to an embodiment of the invention. The cycle lengths are determined and the speed of the scan feed motion is preferably matched to the longest such cycle length. Here, it is particularly preferable for the speed of the scan feed motion to be reduced if it is determined that the cycle length is increased and/or for the speed of the scan feed motion to be increased if it is determined that the cycle length is reduced. In other words, the faster the cycle is, the faster the feed is as well. This orientation with respect to the longest cycle length and the reduction of the speed of the scan feed motion in the case where the cycle length is increased, or vice versa, accommodates the fact that approximately the same number of images of an examination object can always be acquired during a cycle. It is for this reason that the scan feed motion can be accelerated in the case of a higher cycle frequency without the risk of losing image data. Conversely, the feed has to be reduced in the case of a lower frequency.

So as to design an image processing actuation method according to an embodiment of the invention as effectively as possible, in particular to avoid cycle developments being detected too late for a timely change in the scan feed motion, a so-called watch-dog function is used during the imaging scan to analyze the motion signals, which represent the cycle, for arrhythmias, in particular in this application of taking account of the cardiac cycle signals for extrasystolic beats. Within the scope of this watch-dog function, provision can also be made for a time of a next occurrence of a cycle signal to be estimated as a function of a mean value and/or a median of the cycle length of a number of elapsed cycles. Alternatively, to this end, provision can be made for a time of a next occurrence of a cycle signal to be estimated as a function of one or more of the following parameters:

minimum cycle length of a number of elapsed cycles,
maximum cycle length of a number of elapsed cycles,
trend line of a number of elapsed cycles, and
standard deviation of a number of elapsed cycles.

In each of the criteria to be taken into consideration mentioned here, a prediction is made on the basis of an observation of elapsed cycles as to approximately when the next occurrence of a cycle signal is to be expected. By way of example, a cycle signal in this case can be the deflection of an R-wave in an EKG or a similarly prominent point within other motion data representing a cyclic motion.

Within the scope of the image processing actuation method according to an embodiment of the invention for actuating an image processing system, the scan feed motion is particularly preferably controlled using a motion control method according to an embodiment of the invention. This means that that variable input data is input into the image processing in the image processing system which has already lead to the scan feed motion being controlled. Thus, scan feed motion and actuation of the image processing system are not only connected directly, but also simultaneously relate to the same variable input data. Analogously, an image processing actuation module according to the invention is particularly preferably coupled to a motion control module according to the invention in order to determine motion data based on the scan motion control signals.

BRIEF DESCRIPTION OF THE DRAWINGS

In the following text, the invention will once again be explained in more detail with reference to the attached figures and on the basis of example embodiments. Here, the same components are provided with identical reference symbols in the various figures, where.

DETAILED DESCRIPTION OF THE EXAMPLE EMBODIMENTS

Figure 1:
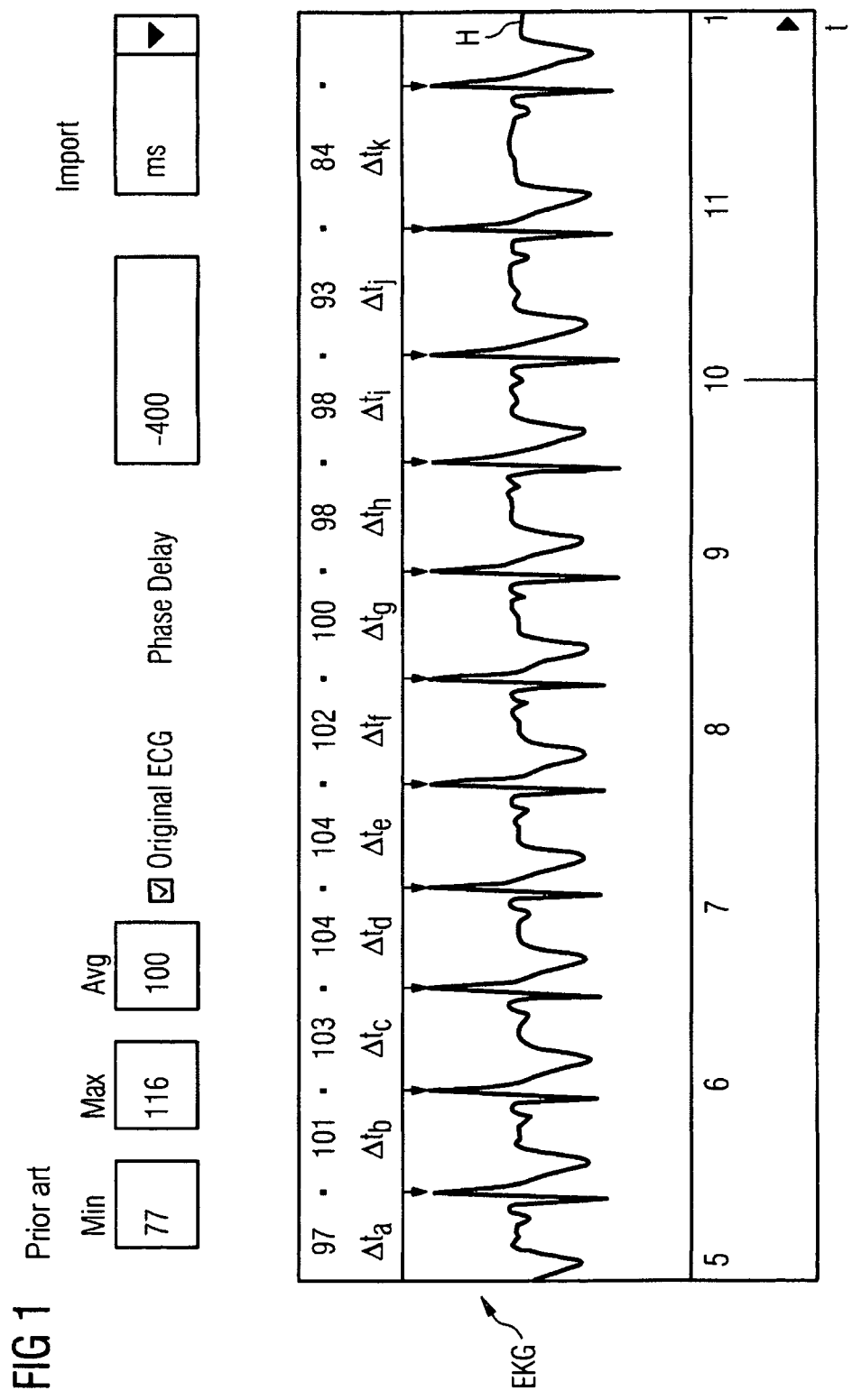
FIG. 1 shows a representative example of an electrocardiogram in accordance with the prior art which serves as a provider of variable input data within the scope of an example embodiment of a motion control method according to the invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a typical electrocardiogram EKG according to the prior art, in which the cardiac curve H of a heart motion is plotted over time t. Here, it can be seen that the heart rate is not uniform, but oscillates between a lower value of 84 heart beats per minute and an upper value of 104 heart beats per minute. The development of every cycle $\Delta t_a$, $\Delta t_b$, $\Delta t_c$, $\Delta t_d$, $\Delta t_e$, $\Delta t_f$, $\Delta t_g$, $\Delta t_h$, $\Delta t_i$, $\Delta t_j$, $\Delta t_k$ compared to its preceding cycles is preferably determined within the scope of a method according to the invention. If there is a change in the frequency of a cycle compared to the preceding cycles, according to the invention, consequences can be derived for the relative scan feed motion of an object bearing device toward a scanner unit.

Figure 2:
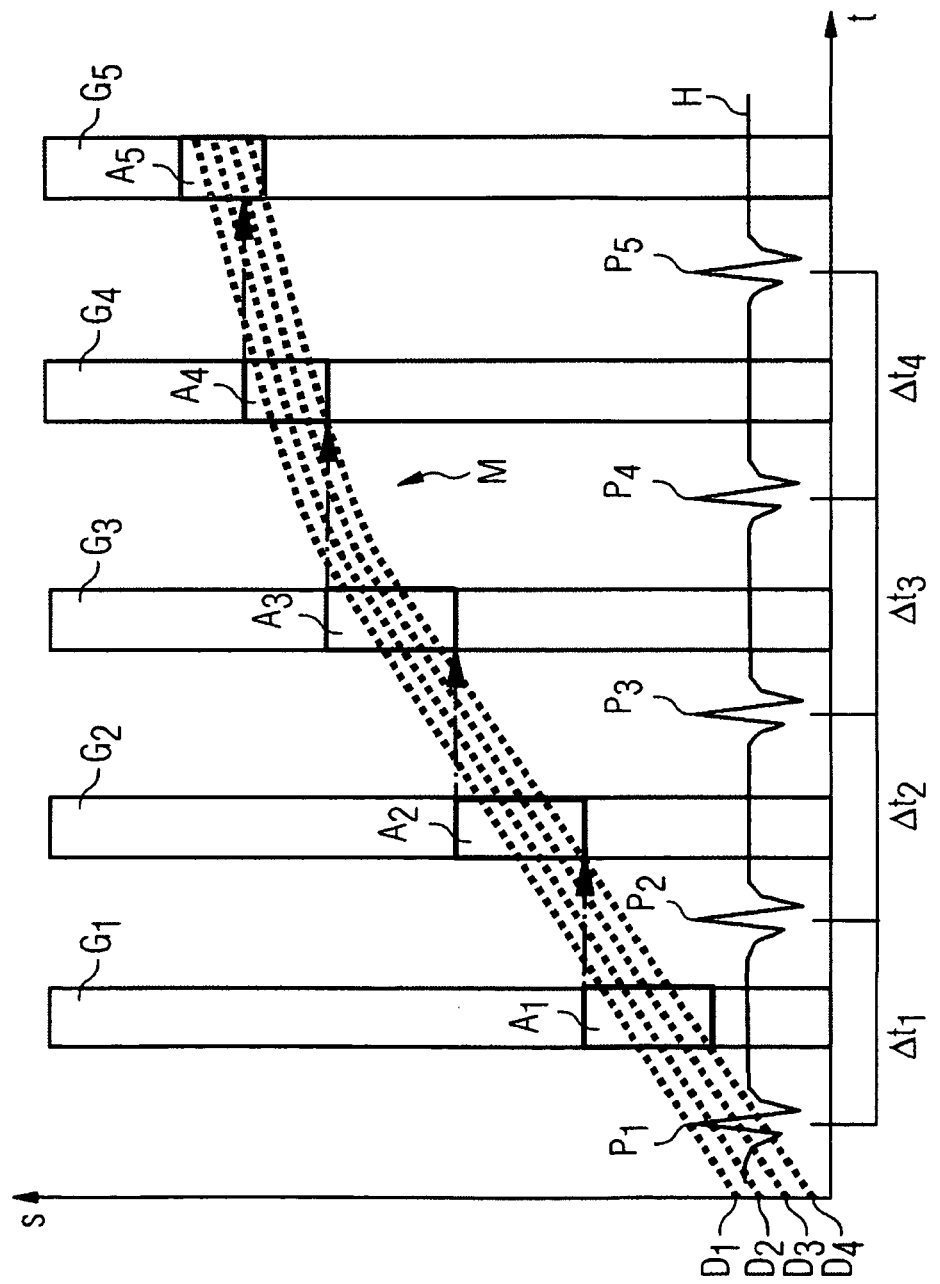
FIG. 2 shows a schematic diagram in which a cardiac curve and positions of detector rows of a detector unit of a computed tomography scanner are put into temporal correlation.

FIG. 2 shows a diagram in which a cardiac curve H is schematically plotted against a time axis t (with arbitrary units and not necessarily to scale). Above it, the path s (in arbitrary units) of four detector rows $D_1$, $D_2$, $D_3$, $D_4$ of an X-ray radiation detector of a computed tomography scanner is in the form of individual points running transversely with respect to the time axis t. The motion of the detector rows $D_1$, $D_2$, $D_3$, $D_4$ representing the scanner feed motion, in combination with their scan rotational motion, effect imaging along four helical profile lines.

Specifically, the region of four cardiac cycles with cycle lengths $\Delta t_1$, $\Delta t_2$, $\Delta t_3$, $\Delta t_4$ is illustrated. They extend between peaks of maximal deflection $P_1$, $P_2$, $P_3$, $P_4$, $P_5$, the so-called R waves of the cardiac curve H. The speed of the scan feed motion is determined from the cardiac curve H. This means that the detector rows $D_1$, $D_2$, $D_3$, $D_4$ of an X-ray detector rotating about an examination object, perpendicularly with respect to the scan feed motion, are displaced with respect to the examination object. On the one hand, this can be achieved by the examination object being moved along the rows of the X-ray detector, i.e. through the scanner unit of the computed tomography scanner, on an object bearing device or by the scanner unit, together with the detector, being moved along an examination object. Thus, the position s of the detector rows $D_1, D_2, D_3, D_4$ is only displaced linearly with time if the heart rate remains constant. Now, the third cycle has a cycle length $\Delta t_3$ which is longer than the preceding cycle lengths $\Delta t_1, \Delta t_2$, i.e. the cycle frequency is reduced. It is for this reason that the scan feed motion is varied. In the present case, its speed is reduced in order to accommodate the lower cycle frequency. The linear motion of the detector rows $D_1, D_2, D_3, D_4$ has a kink in the transition from the third to the fourth cycle, and continues linearly thereafter.

In a further step within the scope of the image post processing of the acquired raw image data from a tomography scan, gating intervals $G_1, G_2, G_3, G_4, G_5$ are derived from the cardiac curve H. They are located in the relative rest phases of the cardiac motion and are therefore directly dependent on the frequency thereof. Now, it has to be ensured that when these gating intervals $G_1, G_2, G_3, G_4, G_5$ are fixed, the position of the object bearing device with respect to the scanner unit is also taken into account. This is related to the fact that the spatial covers $A_1, A_2, A_3, A_4, A_5$ of the examination object correlate with respect to one another as a result of the detector rows $D_1, D_2, D_3, D_4$ within the gating intervals $G_1, G_2, G_3, G_4, G_5$ such that every single location of the examination object can be imaged. The fact that this is the case here is indicated by the arrows between cover regions $A_1, A_2, A_3, A_4, A_5$. The upper end of the cover region $A_1$ is at approximately the same level as the bottom end of the subsequent cover region $A_2$. The variation of the scanner speed as a function of the cardiac curve H in turn only makes it possible that the cover $A_4$ adjoins the preceding cover $A_3$ and there is no break in the coverage despite the heart rate which is reduced compared to the preceding cardiac cycles. Thus, this image clarifies the fact that in addition to the motion control method, in which the scan feed motion is varied on the basis of the cardiac curve H, the image processing of the raw image data is also effected with the aid of the actuation method according to the invention as a function of the scan feed motion or the cardiac curve H which also defines the scan feed motion.

Figure 3:
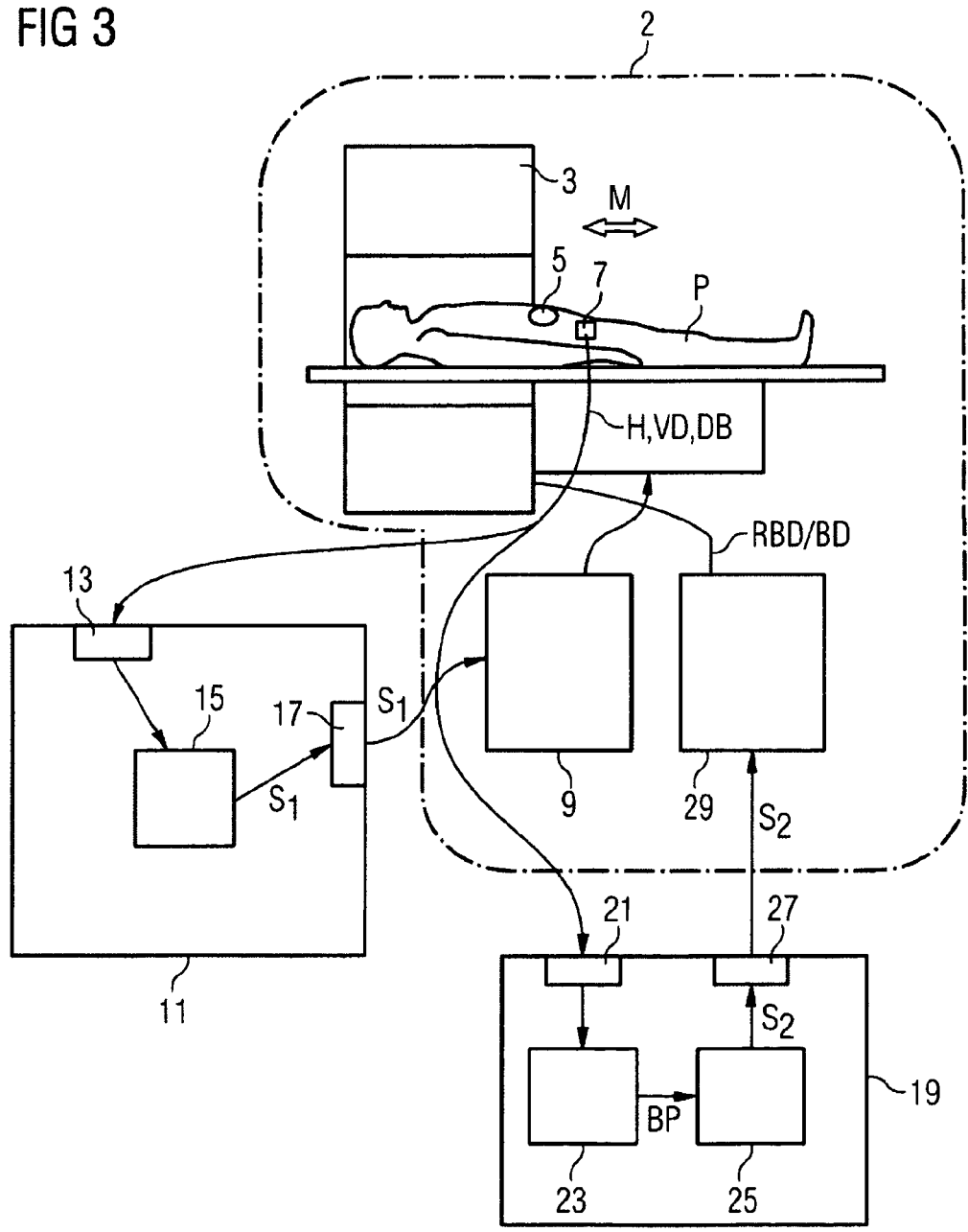
FIG. 3 shows a schematic block diagram of a computed tomography system with a motion control module according to an embodiment of the invention and an image processing actuation module according to an embodiment of the invention.

FIG. 3 shows, in a schematic block illustration, a computed tomography system 2 and exemplary embodiments of a motion control module 11 according to an embodiment of the invention and an image processing actuation module 19 according to an embodiment of the invention.

Inter alia, the computed tomography system 2 comprises an object bearing device 1 and a scanner unit 3 which can be moved toward and away from each other. Here, it is irrelevant within the scope of the invention whether—as in the present case—the object bearing device 1 moves toward the scanner unit 3 or whether the scanner unit 3 can be displaced in the direction of the object bearing device 1. In both cases this results in a scan feed motion M.

Furthermore, the computed tomography system 2 comprises a control device 9 for the object bearing device 1 and an image processing system 29. The control device 9 is used to control the scan feed motion M, while the image processing system 29 prepares raw image data RBD or partially processed image data BD to form an optimized display.

The object bearing device 1 bears a patient P with an examination object 5 which in this case is the heart. Using a measuring instrument 7, in this case an EKG probe, variable input data VD, in this case a cardiac curve H, can be derived and passed on to the motion control module 11 and the image processing control module 19.

The motion control module 11 comprises an input interface 13 for the variable input data VD and an output interface 17 for outputting scan motion control signals $S_1$ to the control device 9. A control command generation unit 15 is arranged therebetween in the form of a software module on a processor and derives scan motion control signals $S_1$ for controlling the scan feed motion M. This feed motion M is controlled by the control device 9. The scan motion control signals $S_1$ are derived as a function of the variable input data VD, that is to say the cardiac curve H in this case.

The image processing actuation module 19 receives motion data DB, in this case again the cardiac curve H, via an input interface 21 and passes image processing control signals $S_2$ on to the image processing system 29 via an output interface 27. Said image processing system 29 carries out gating on the basis of the image processing control signals $S_2$, as explained above.

A motion profile generation unit 23 for generating a motion profile BP from the motion data DB and a control signal generation unit 25 for deriving image processing control signals $S_2$ from the motion profile BP are arranged between the two interfaces 21, 27. Thus, the cardiac curve H serves as a possible type of motion data BD related to the relative scan feed motion M. Alternatively, the scan feed motion M can for example also be measured directly and motion data DB can be derived therefrom. The motion profile BP is generated from the motion data DB by the motion profile generation unit 23 and control signals $S_2$, which can be passed on to the image processing system 29, are derived therefrom by way of the control signal generation unit 25. In particular, such image processing control signals $S_2$ are signals which define the start time and end time of a gating interval.

Finally, reference is once again made to the fact that the method described in detail above and the illustrated apparatuses are only example embodiments which can be modified by a person skilled in the art in very different ways without departing from the field of the invention. Furthermore, the use of the indefinite articles "a" or "an" does not preclude the possibility of the relevant features being present a number of times.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A motion control method for controlling a relative scan feed motion of an object bearing device toward a scanner unit of a computed tomography system during a helical tomography scan of a heart carrying out a substantially cyclical object motion, the motion control method comprising:
   generating scan motion control signals parallel to the relative scan feed motion to control the relative scan feed motion, the scan motion control signals being derived from variable input data obtained in parallel during the helical tomography scan, the variable input data including motion signals which represent the object motion cycle determined with aid of an electrocardiogram, wherein a speed of the relative scan feed motion is reduced upon an extrasystole being detected, the reduced speed being greater than zero and maintained at a non-zero speed.

2. The motion control method as claimed in claim 1, wherein a dependence of the relative scan feed motion on the variable input data is fixed in advance in one or more rules.

3. The motion control method as claimed in claim 1, wherein cycle lengths of the object motion are determined and the speed of the relative scan feed motion is matched to a relatively longest of the cycle lengths.

4. The motion control method as claimed in claim 3, wherein the speed of the relative scan feed motion is reduced upon determining that the cycle lengths are determined to have increased, and the speed of the relative scan feed motion is increased upon determining that the cycle lengths have decreased.

5. The motion control method as claimed in claim 1, wherein, in order to detect cycle developments, a time of a next occurrence of a cycle signal is estimated as a function of at least one of a mean value and a median of a cycle length of a number of elapsed cycles.

6. The motion control method as claimed in claim 1, wherein in order to detect cycle developments, a time of a next occurrence of a cycle signal is estimated as a function of one or more of the following parameters:
   minimum cycle length of a number of elapsed cycles,
   maximum cycle length of a number of elapsed cycles,
   trend line of a number of elapsed cycles, and
   standard deviation of a number of elapsed cycles.

7. A non-transitory computer readable medium encoded with a computer program product which can be directly loaded into at least one of a programmable motion control module and an image processing actuation module, the computer program product including program code sections to execute all steps of the motion control method as claimed in claim 1 upon the program being executed in the at least one of the motion control module and the image processing actuation module.

8. A non-transitory computer readable medium including program segments for, when executed on a computer device, causing the computer device to implement the method of claim 1.

9. An image processing actuation method for actuating an image processing system of a computed tomography system in which at least one of raw image data acquired by the computed tomography system and image data of an examination object derived therefrom are processed, the image processing actuation method comprising:
   recording motion data connected to a relative scan feed motion of an object bearing device toward a scanner unit of a computed tomography system;
   generating a motion profile from the recorded motion data; and
   generating image processing control signals from the motion profile, the image processing control signals being used as a control input for the image processing system, wherein the relative scan feed motion is controlled by generating scan motion control signals parallel to the relative scan feed motion to control the relative scan feed motion, the scan motion control signals being derived from variable input data obtained in parallel during a tomography scan, the variable input data including motion signals which represent the object motion cycle determined with an aid of an electrocardiogram, wherein a speed of the relative scan feed motion is reduced upon an extrasystole being detected, the reduced speed being greater than zero and maintained at a non-zero speed.

10. A non-transitory computer readable medium encoded with a computer program product which can be directly loaded into at least one of a programmable motion control module and an image processing actuation module, the computer program product including program code sections to execute all steps of the image processing actuation method as claimed in claim 9 upon the program being executed in the at least one of the motion control module and the image processing actuation module.

11. A non-transitory computer readable medium including program segments for, when executed on a computer device, causing the computer device to implement the method of claim 9.

12. A motion control module for controlling a relative scan feed motion of an object bearing device toward a scanner unit of a computed tomography system for performing a helical tomography scan of a heart carrying out a substantially cyclical object motion, the motion control module comprising:
- an input interface configured to input variable input data including motion signals which represent the object motion cycle determined with an aid of an electrocardiogram;
- a control command generation unit configured to derive, during operation, scan motion control signals for controlling the relative scan feed motion as a function of the variable input data; and
- an output interface configured to output the scan motion control signals to a control device for at least one of the object bearing device and the scanner unit, wherein the motion control module is designed such that a speed of the relative scan feed motion is reduced upon an extrasystole being detected, the reduced speed being greater than zero and maintained at a non-zero speed.

13. An image processing actuation module for actuating an image processing system of a computed tomography system in which at least one of raw image data acquired during operation by the computed tomography system and image data of an examination object carrying out a cyclical object motion derived therefrom are processed to be optimized for imaging, the image processing actuation module comprising:
- an input interface for motion data, connected to a relative scan feed motion of an object bearing device toward a scanner unit of a computed tomography system;
- a motion profile generation unit configured to generate a motion profile from the motion data;
- a control signal generation unit configured to derive image processing control signals from the generated motion profile; and
- an output interface configured to output the image processing control signals to the image processing system, wherein the image processing actuation module is coupled to a motion control module as claimed in claim 12 so as to determine motion data on a basis of the scan motion control signals.

14. A motion control method for controlling a relative scan feed motion of an object bearing device toward a scanner unit of a computed tomography system during a helical tomography scan of a heart carrying out a substantially cyclical object motion, the motion control method comprising:
- generating scan motion control signals parallel to the relative scan feed motion to control the relative scan feed motion, the scan motion control signals being derived from variable input data obtained in parallel during the helical tomography scan, the variable input data including motion signals which represent the object motion cycle determined with an aid of an electrocardiogram; and
- detecting whether or not an extrasystole is present; and
- reducing, a speed of the relative scan feed motion upon an extrasystole being detected, the reduced speed being greater than zero and maintained at a non-zero speed.

15. The motion control method as claimed in claim 14, wherein a dependence of the relative scan feed motion on the variable input data is fixed in advance in one or more rules.

16. The motion control method as claimed in claim 14, wherein cycle lengths of the object motion are determined and the speed of the relative scan feed motion is matched to a relatively longest of the cycle lengths.

17. The motion control method as claimed in claim 16, wherein the speed of the relative scan feed motion is reduced upon determining that the cycle lengths are determined to have increased, and the speed of the relative scan feed motion is increased upon determining that the cycle lengths have decreased.

18. The motion control method as claimed in claim 14, wherein, in order to detect cycle developments, a time of a next occurrence of a cycle signal is estimated as a function of at least one of a mean value and a median of a cycle length of a number of elapsed cycles.

19. The motion control method as claimed in claim 14, wherein in order to detect cycle developments, a time of a next occurrence of a cycle signal is estimated as a function of one or more of the following parameters:
- minimum cycle length of a number of elapsed cycles,
- maximum cycle length of a number of elapsed cycles,
- trend line of a number of elapsed cycles, and
- standard deviation of a number of elapsed cycles.

20. A non-transitory computer readable medium encoded with a computer program product which can be directly loaded into at least one of a programmable motion control module and an image processing actuation module, the computer program product including program code sections to execute all steps of the motion control method as claimed in claim 14 upon the program being executed in the at least one of the motion control module and the image processing actuation module.

21. A non-transitory computer readable medium including program segments for, when executed on a computer device, causing the computer device to implement the method of claim 14.

* * * * *